United States Patent
Choi

(10) Patent No.: US 9,949,044 B1
(45) Date of Patent: Apr. 17, 2018

(54) BINAURAL HEARING AID WITH MULTI FUNCTIONS

(71) Applicant: Sorynorydotcom Inc., Suwon-si (KR)

(72) Inventor: Yong Il Choi, Yongin-si (KR)

(73) Assignee: Sorynorydotcom Inc., Suwon-si (KR)

( * ) Notice: Subject to any disclaimer, the term of this patent is extended or adjusted under 35 U.S.C. 154(b) by 0 days.

(21) Appl. No.: 15/296,327

(22) Filed: Oct. 18, 2016

(30) Foreign Application Priority Data

Oct. 17, 2016 (KR) .................. 10-2016-0134414

(51) Int. Cl.
*H04R 25/00* (2006.01)
*A61B 5/024* (2006.01)
*A61B 5/00* (2006.01)

(52) U.S. Cl.
CPC ....... *H04R 25/552* (2013.01); *A61B 5/02433* (2013.01); *A61B 5/6815* (2013.01); *H04R 25/305* (2013.01); *H04R 25/505* (2013.01); *H04R 25/554* (2013.01)

(58) Field of Classification Search
CPC ............ H04R 25/552; H04R 2225/021; H04R 2225/023; H04R 2225/025; H04R 2460/12; H04R 2225/55; H04R 25/456
USPC .......... 381/23, 23.1, 315, 312, 316; 455/425
See application file for complete search history.

(56) References Cited

U.S. PATENT DOCUMENTS

| 8,300,864 B2 * | 10/2012 | Mullenborn | H04R 25/554 381/312 |
|---|---|---|---|
| 8,989,394 B2 | 3/2015 | Cho et al. | |
| 2002/0076073 A1 * | 6/2002 | Taenzer | H04R 25/502 381/315 |
| 2005/0090295 A1 * | 4/2005 | Ali | H03G 9/005 455/575.2 |
| 2015/0109125 A1 * | 4/2015 | Kaib | A61N 1/3993 340/539.12 |
| 2015/0124976 A1 | 5/2015 | Pedersen et al. | |
| 2016/0073204 A1 * | 3/2016 | Solum | H04R 25/558 381/315 |
| 2016/0094923 A1 * | 3/2016 | Jensen | H04R 25/75 600/28 |

FOREIGN PATENT DOCUMENTS

| KR | 10-1209126 B1 | 12/2012 |
|---|---|---|
| KR | 10-2015-0020874 A | 2/2015 |

OTHER PUBLICATIONS

Korean Office Action dated May 22, 2017 in corresponding Korean Patent Application No. 10-2016-0134414 (4 pages in Korean).

\* cited by examiner

Primary Examiner — Melur Ramakrishnaiah
(74) Attorney, Agent, or Firm — NSIP Law

(57) ABSTRACT

The present invention relates to a binaural hearing aid with multiple functions in which multiple functions such as a wireless headset function, a measuring pulse function, a pulse information transmitting function, etc. in addition to a hearing aid function are implemented to improve user convenience.

12 Claims, 4 Drawing Sheets

BINAURAL HEARING AID WITH MULTI FUNCTIONS

CROSS-REFERENCE TO RELATED APPLICATION(S)

This application claims priority from Korean Patent Application No. 10-2016-0134414, filed on Oct. 17, 2016, in the Korean Intellectual Property Office, the disclosure of which is incorporated herein by reference in its entirety.

BACKGROUND

1. Field

The following description relates to a hearing aid, and more particularly, a binaural hearing aid.

2. Description of Related Art

Korean Laid-open Patent Application No. 10-2015-0020874 (Feb. 27, 2015) suggests a hearing aid with a binaural hearing aid function, including a hearing aid module including a microphone, a digital signal processor, a synchronization unit, and a transmission unit, and an assistant device including a reception unit configured to receive a signal transmitted from the transmission unit and a receiver configured to deliver the signal transmitted from the reception unit to a user, wherein the hearing aid module and the assistant device are synchronized by the synchronization unit, and a signal having a delay time according to a transmission distance is delivered to the user's ears.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

The following description relates to a binaural hearing aid with multiple functions including a wireless headset function in addition to a hearing aid function.

The following description also relates to a binaural hearing aid with multiple functions including a pulse measuring function and a pulse information transmitting function in addition to a hearing aid function.

In one general aspect, a binaural hearing aid includes a master hearing aid and a slave hearing aid, and the master hearing aid includes: a microphone configured to receive an analog audio signal from the outside; a signal processing unit configured to amplify the analog audio signal input by the microphone, perform automatic gain control and AD conversion, and output the result; a first wireless communication unit configured to receive a digital audio signal from a smart device using a first wireless communication protocol; an ear speaker configured to output a digital audio signal for a hearing aid output by the signal processing unit or output a digital audio signal for a wireless headset received by the first wireless communication unit; and a control unit configured to control performance of a hearing aid function performed by the signal processing unit and a wireless headset function performed by the first wireless communication unit.

The master hearing aid may further include a second wireless communication unit configured to transmit the digital audio signal for the wireless headset received by the first wireless communication unit to the slave hearing aid using a second wireless communication protocol.

The slave hearing aid may include: a microphone configured to receive an analog audio signal from the outside; a signal processing unit configured to amplify the analog audio signal input by the microphone, perform automatic gain control and AD conversion, and output the result; a second wireless communication unit configured to receive a digital audio signal from the master hearing aid using a second wireless communication protocol; an ear speaker configured to output a digital audio signal for a hearing aid output by the signal processing unit or output a digital audio signal for a wireless headset received by the second wireless communication unit; and a control unit configured to control performance of a hearing aid function performed by the signal processing unit and a wireless headset function performed by the second wireless communication unit.

The slave hearing aid may further include: a pulse measuring device configured to measure a pulse of a user; and a memory configured to locally store pulse information measured by the pulse measuring device.

The control unit of the slave hearing aid may perform a pulse measuring function of performing control such that the pulse of the user is measured using the pulse measuring device, and the pulse information of the user is stored and accumulated in the memory.

The control unit of the slave hearing aid may perform a pulse information transmitting function of performing control such that the pulse information stored in the memory is read, and the pulse information is transmitted to the master hearing aid through the second wireless communication unit of the slave hearing aid.

The control unit of the master hearing aid may perform a pulse information transmitting function of performing control such that the pulse information transmitted from the slave hearing aid is received through the second wireless communication unit of the master hearing aid, and the pulse information is transmitted to the smart device through the first wireless communication unit.

The control unit of the master hearing aid may control delay of an output of the digital audio signal for the wireless headset of the ear speaker of the master hearing aid to synchronize the output of the digital audio signal for the wireless headset of the ear speaker of the master hearing aid and the output of the digital audio signal for the wireless headset of the ear speaker of the slave hearing aid.

The control unit of the master hearing aid may perform control such that the hearing aid function of the master hearing aid is stopped when a first wireless communication function is activated.

The control unit of the master hearing aid may transmit an instruction to stop the hearing aid function of the slave hearing aid to the slave hearing aid through the second wireless communication unit of the master hearing aid when the first wireless communication function is activated.

The control unit of the slave hearing aid may perform control such that the hearing aid function of the slave hearing aid is stopped when the instruction to stop the hearing aid function of the slave hearing aid is received.

The control unit of the slave hearing aid may control a pulse measurement period of the pulse measuring device by comparing a state of charge of a battery of the master hearing aid with a state of charge of a battery of the slave hearing aid.

The master hearing aid or the slave hearing aid may further include an audio mixer configured to amplify or reduce the digital audio signal for the hearing aid or the digital audio signal for the wireless headset by a frequency channel and output the result.

Other features and aspects will be apparent from the following detailed description, the drawings, and the claims.

Figure 1:
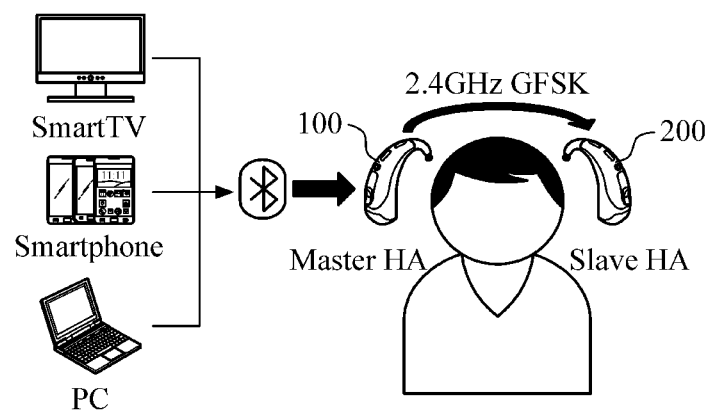
FIG. 1 is a schematic diagram illustrating a binaural hearing aid with multiple functions according to an embodiment of the present invention.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, exemplary embodiments of the present invention will be described in detail with reference to the accompanying drawings so as to enable one skilled in the art to which the present invention pertains to easily carry out.

Further, in the following description of the present invention, a detailed description of known functions and configurations incorporated herein will be omitted when it may make the subject matter of the present invention rather unclear.

As terminology used herein, general terms currently in wide use are selected wherever possible in consideration of functions in the present disclosure, but may vary according to intentions of those of ordinary skill in the art, precedent cases, the advent of new technology, and so on. Therefore, the terms used in this specification should be defined based on the meanings of the terms together with the description throughout the specification rather than their simple names.

FIG. 1 is a schematic diagram illustrating a binaural hearing aid with multiple functions according to an embodiment of the present invention. As illustrated in FIG. 1, the binaural hearing aid with multiple functions according to the embodiment of the present invention includes a master hearing aid 100 and a slave hearing aid 200.

The master hearing aid 100 is wearable on one ear of the user, and the slave hearing aid 200 is wearable on the other ear of the user. The master hearing aid 100 may communicate with smart devices such as a smartphone, a smart TV, a laptop computer, etc. using a first wireless communication protocol. The slave hearing aid 200 may communicate with the master hearing aid 100 using a second wireless communication protocol.

For example, the first wireless communication protocol may be a Bluetooth communication protocol, and the second wireless communication protocol may be a Gaussian frequency-shift keying (GFSK) communication protocol that is a type of frequency-shift keying.

Figure 2:
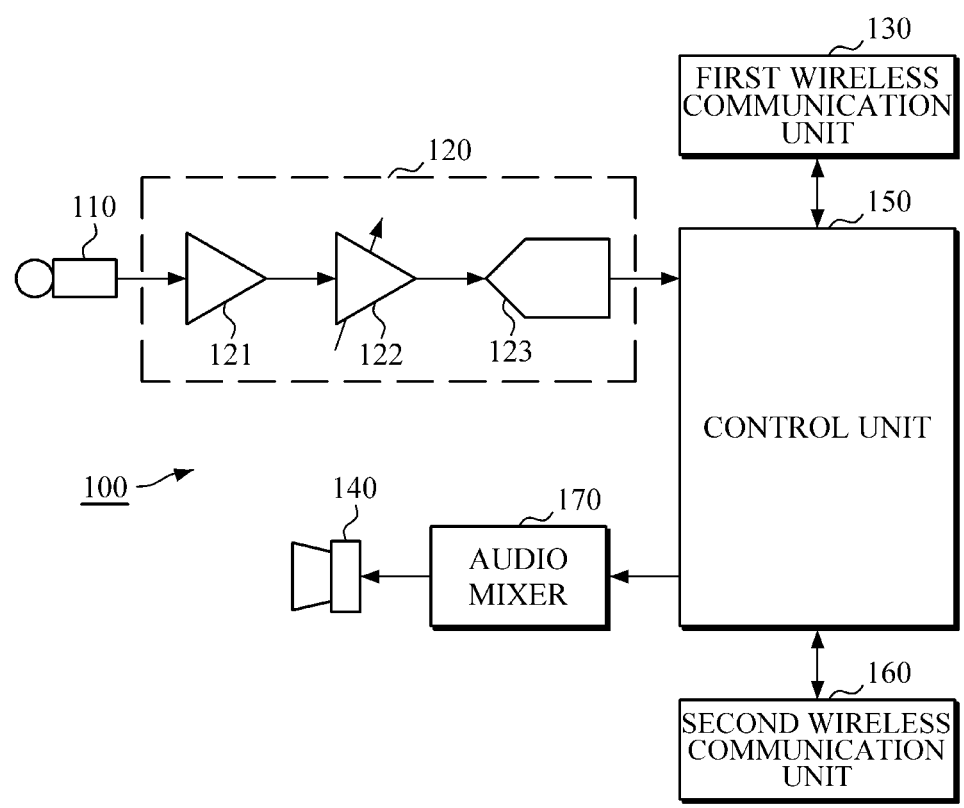
FIG. 2 is a diagram illustrating an example of a master hearing aid of the binaural hearing aid with multiple functions according to the embodiment of the present invention.

FIG. 2 is a diagram illustrating an example of a master hearing aid of the binaural hearing aid with multiple functions according to the embodiment of the present invention. As illustrated in FIG. 2, the master hearing aid 100 according to the embodiment of the present invention includes a microphone 110, a signal processing unit 120, a first wireless communication unit 130, an ear speaker 140, and a control unit 150.

The microphone 110 receives an analog audio signal from the outside. The analog audio signal within an audible frequency band that is generated near the user is input to the master hearing aid 100 through the microphone 110.

The signal processing unit 120 amplifies the analog audio signal input by the microphone 110, performs automatic gain control and analog to digital (AD) conversion, and outputs the result.

For example, the signal processing unit 120 may include an amplifier 121 which amplifies the analog audio signal input by the microphone and outputs the result, an automatic gain controller (AGC) 122 which automatically controls gain of the analog audio signal amplified by the amplifier, and an AD converter 123 which converts the analog audio signal, of which gain is controlled by the AGC, into a digital audio signal.

The first wireless communication unit 130 receives the digital audio signal from smart devices such as a smartphone, a smart TV, a laptop computer, etc. using the first wireless communication protocol. In this case, the first wireless communication protocol may be a Bluetooth communication protocol.

For example, a smart device having a Bluetooth communication function is set to communicate with the master hearing aid 100 which is found by searching for Bluetooth devices near the smart device via Bluetooth communication so that bidirectional wireless communication between the smart device and the master hearing aid 100 may be established.

The ear speaker 140 outputs a digital audio signal for a hearing aid output by the signal processing unit 120, or a digital audio signal for a wireless headset received by the first wireless communication unit 130. For example, the ear speaker 140 may be a digital speaker which is manufactured to be inserted into an earhole.

The control unit 150 controls performance of a hearing aid function performed by the signal processing unit 120 and a wireless headset function performed by the first wireless communication unit 130. For example, the control unit 150 may perform control such that the digital audio signal for the hearing aid processed by the signal processing unit 120 is output through the ear speaker 140 in a hearing aid mode and the digital audio signal for the wireless headset received by the first wireless communication unit 130 is output through the ear speaker 140 in a wireless headset mode.

In the present invention, the master hearing aid of the binaural hearing aid with multiple functions includes a wireless headset function in addition to a hearing aid function so that the user can listen to music played on the smart device and make a call in a hands-free mode through the master hearing aid of the binaural hearing aid with multiple functions, thus improving user convenience.

According to an additional aspect of the present invention, the master hearing aid 100 may further include a second wireless communication unit 160. The second wireless communication unit 160 transmits the digital audio signal for the wireless headset received by the first wireless communication unit 130 to the slave hearing aid 200 using the second wireless communication protocol. In this case, the second wireless communication protocol may be a GFSK communication protocol that is a type of frequency-shift keying.

According to the embodiment of the present invention, the master hearing aid 100 transmits the digital audio signal for the wireless headset, which is received from the smart device by the first wireless communication unit 130, to the slave hearing aid 200 through the second wireless communication unit 160 such that the slave hearing aid of the binaural hearing aid with multiple functions performs a wireless headset function in addition to the hearing aid function.

Accordingly, the user can listen to music played on the smart device and make a call in a hands-free mode through the slave hearing aid of the binaural hearing aid with multiple functions, and thus user convenience can be improved.

Figure 3:
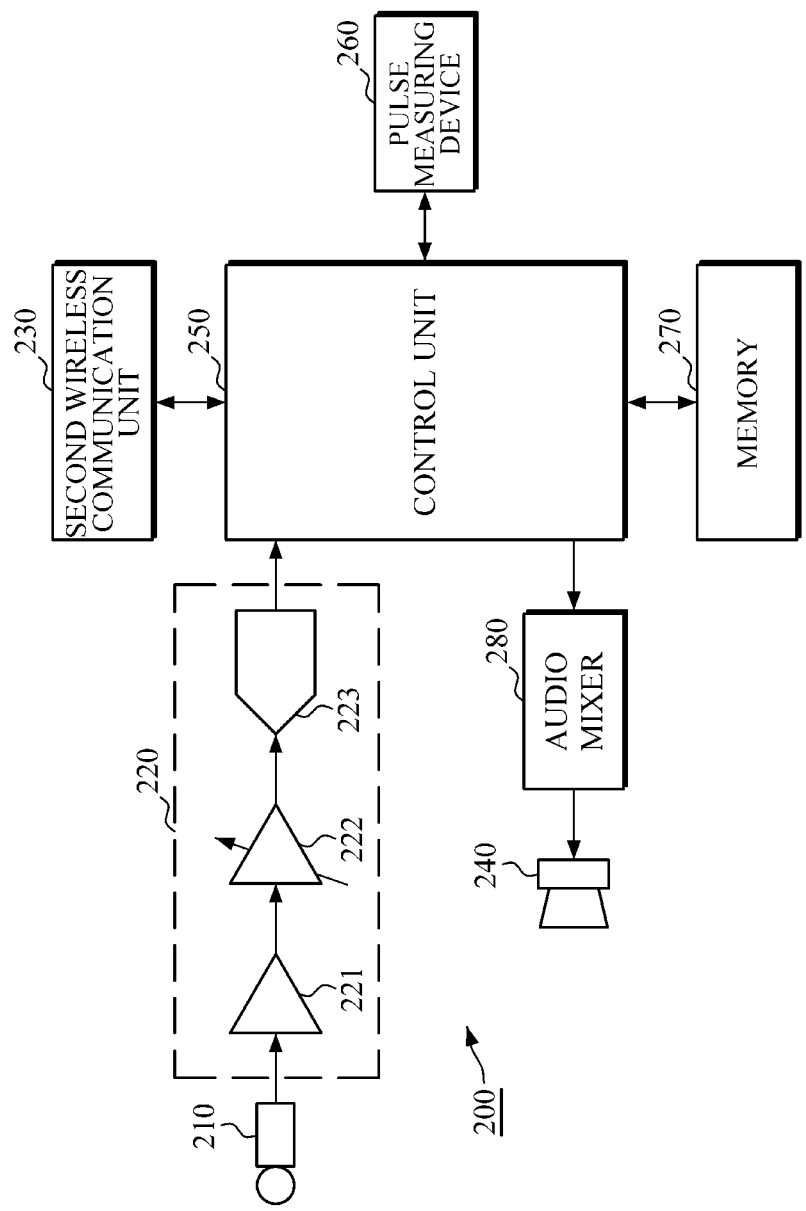
FIG. 3 is a diagram illustrating an example of a slave hearing aid of the binaural hearing aid with multiple functions according to the embodiment of the present invention.

FIG. 3 is a diagram illustrating an example of a slave hearing aid of the binaural hearing aid with multiple functions according to the embodiment of the present invention. As illustrated in FIG. 3, the slave hearing aid 200 according to the embodiment of the present invention includes a microphone 210, a signal processing unit 220, a second wireless communication unit 230, an ear speaker 240, and a control unit 250.

The microphone 210 receives an analog audio signal from the outside. The analog audio signal with in an audible frequency band that is generated near the user is input to the slave hearing aid 200 through the microphone 210.

The signal processing unit 220 amplifies the analog audio signal input by the microphone 210, performs automatic gain control and AD conversion, and outputs the result.

For example, the signal processing unit 220 may include an amplifier 221 which amplifies the analog audio signal input by the microphone, an AGC 222 which automatically controls gain of the analog audio signal amplified by the amplifier, and an AD converter 223 which converts the analog audio signal, of which gain is controlled by the AGC, into a digital audio signal.

The second wireless communication unit 230 receives the digital audio signal from the master hearing aid 100 using the second wireless communication protocol. In this case, the second wireless communication protocol may be a GFSK communication protocol that is a type of frequency-shift keying.

For example, the master hearing aid 100 and the slave hearing aid 200 are set to be connected via GFSK communication to establish bidirectional wireless communication between the master hearing aid 100 and the slave hearing aid 200 so that the second wireless communication unit 230 of the slave hearing aid 200 may receive the digital audio signal transmitted from the master hearing aid 100.

The ear speaker 240 outputs a digital audio signal for a hearing aid output by the signal processing unit 220, or a digital audio signal for a wireless headset received by the second wireless communication unit 230. For example, the ear speaker 240 may be a digital speaker which is manufactured to be inserted into an earhole.

The control unit 250 controls performance of a hearing aid function performed by the signal processing unit 220 and a wireless headset function performed by the second wireless communication unit 230. For example, the control unit 250 may perform control such that the digital audio signal for the hearing aid processed by the signal processing unit 220 is output through the ear speaker 240 in a hearing aid mode and the digital audio signal for the wireless headset received by the second wireless communication unit 230 is output through the ear speaker 240 in a wireless headset mode.

In the present invention, the slave hearing aid of the binaural hearing aid with multiple functions includes a wireless headset function in addition to a hearing aid function so that the user can listen to music played on the smart device and make a call in a hands-free mode through the slave hearing aid of the binaural hearing aid with multiple functions, thus improving user convenience.

According to an additional aspect of the present invention, the slave hearing aid 200 may further include a pulse measuring device 260 which measures a pulse of the user and a memory 270 in which pulse information measured by the pulse measuring device 260 is stored locally.

Figure 4:
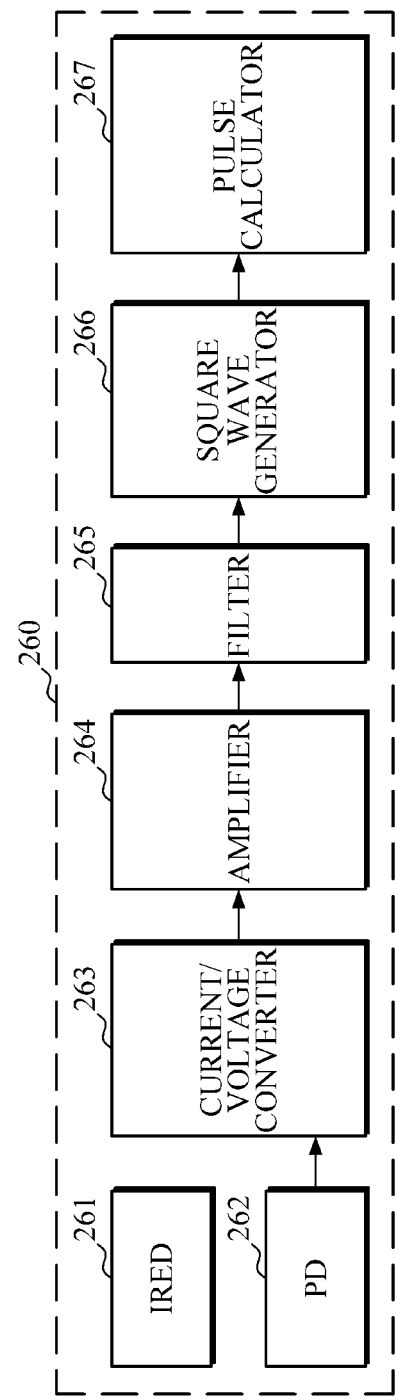
FIG. 4 is a diagram illustrating an example of a pulse measuring device implemented in the slave hearing aid of the binaural hearing aid with multiple functions according to the embodiment of the present invention.

FIG. 4 is a diagram illustrating an example of a pulse measuring device implemented in the slave hearing aid of the binaural hearing aid with multiple functions according to the embodiment of the present invention. As illustrated in FIG. 4, the pulse measuring device 260 according to the embodiment of the present invention includes an infrared emitting diode (IRED) 261, a photo diode (PD) 262, a current/voltage converter 263, an amplifier 264, a filter 265, a square wave generator 266 and a pulse calculator 267.

The IRED 261 radiates infrared light (IR) to skin at a rear side of the user's ear. The PD 262 receives the IR reflected from the skin at the rear side of the user's ear and outputs a signal of a current component according to the amount of the received IR.

The current/voltage converter 263 converts the signal of the current component output from the PD 262 into a signal of a voltage component. The amplifier 264 amplifies the signal of the voltage component output from the current/voltage converter 263.

The filter 265 filters noise included in the signal of the voltage component that is amplified by the amplifier 264. The square wave generator 266 compares the signal of the voltage component from which the noise is filtered by the filter 265 with a signal of a standard level and outputs a square wave according to the difference of the signals.

The pulse calculator 267 calculates the pulse by counting the number of square waves output by the square wave generator 266 per minute and stores the pulse information in the memory 270. Accordingly, the user's pulse information measured by the pulse measuring device 260 is stored and accumulated in the memory 270.

According to an additional aspect of the present invention, the control unit 250 of the slave hearing aid 200 may be implemented to perform a function of transmitting the pulse information which performs control such that the pulse information stored in the memory 270 is read and the pulse information is transmitted to the master hearing aid 100 through the second wireless communication unit 230 of the slave hearing aid 200.

Accordingly, the pulse information of the user which is measured by the pulse measuring device 260 of the slave hearing aid 200 without a function of communicating with the smart device and stored in the memory 270 is transmitted to the master hearing aid 100 with a function of communicating with a smart device.

According to an additional aspect of the present invention, the control unit 150 of the master hearing aid 100 may be implemented to perform a function of transmitting the pulse information which performs control such that the pulse information transmitted from the slave hearing aid 200 is received through the second wireless communication unit 160 of the master hearing aid 100 and transmitted to the smart device through the first wireless communication unit 130.

Accordingly, the master hearing aid 100 which receives the pulse information of the user transmitted from the slave hearing aid 200 without the function of communicating with the smart device may transmit the pulse information to the smart device.

The smart device can be applied for healthcare, for example, by analyzing big data using the pulse information of the user received from the master hearing aid 100 to anticipate abnormalities in the user's heartbeat.

According to an additional aspect of the present invention, the control unit 150 of the master hearing aid 100 may be implemented to control delay of an output of the digital audio signal for the wireless headset of the ear speaker 140 of the master hearing aid 100 to synchronize the output of the digital audio signal for the wireless headset of the ear speaker 140 of the master hearing aid 100 and an output of the digital audio signal for the wireless headset of the ear speaker 240 of the slave hearing aid 200.

Since the digital audio signal for the wireless headset is transmitted to the second wireless communication unit 230 of the slave hearing aid 200 through the second wireless communication unit 160 of the master hearing aid 100, transmission delay is caused.

When a phase difference of the output of the digital audio signal for the wireless headset due to the transmission delay is not corrected, the digital audio signal for the wireless headset may be output later in the ear speaker 240 of the slave hearing aid 200 than the ear speaker 140 of the master hearing aid 100.

Therefore, the phase difference of the output of the digital audio signal for the wireless headset due to the transmission delay is resolved by controlling delay of the output of the digital audio signal for the wireless headset of the ear speaker 140 of the master hearing aid 100 through the control unit 150 of the master hearing aid 100 for a certain time.

The delay time is calculated by looping back the signal for time synchronization through the second wireless communication between the master hearing aid 100 and the slave hearing aid 200 to synchronize the output of the digital audio signal for the wireless headset of the ear speaker 140 of the master hearing aid 100 and the output of the digital audio signal for the wireless headset of the ear speaker 240 of the slave hearing aid 200, and the output of the digital audio signal for the wireless headset of the ear speaker 140 of the master hearing aid 100 is delayed as much as the calculated delay time.

According to an additional aspect of the present invention, the control unit 150 of the master hearing aid 100 performs control such that the hearing aid function of the master hearing aid 100 is stopped when the first wireless communication function is activated.

In this case, the control unit 150 of the master hearing aid 100 may be implemented to transmit an instruction to stop the hearing aid function of the slave hearing aid to the slave hearing aid 200 through the second wireless communication unit 160 of the master hearing aid when the first wireless communication function is activated.

Then, the control unit 250 of the slave hearing aid 200 stops the hearing aid function of the slave hearing aid when the instruction to stop the hearing aid function of the slave hearing aid is received.

This is an embodiment of stopping the hearing aid function in the wireless headset mode, because if the digital audio signal for the hearing aid and the digital audio signal for the wireless headset are output at the same time when the first wireless communication function is activated, that is, in the wireless headset mode, the digital audio signal for the hearing aid may interrupt listening of the digital audio signal for the wireless headset.

According to an additional aspect of the present invention, the control unit 250 of the slave hearing aid 200 may control a pulse measurement period of the pulse measuring device 260 by comparing a state of charge of a battery (not shown in the drawings) of the master hearing aid 100 with a state of charge of a battery (not shown in the drawings) of the slave hearing aid 200.

The master hearing aid 100 and the slave hearing aid 200 are operated separately using a battery such as a mercury battery, and when the pulse measuring device 260 of the slave hearing aid 200 wakes up to measure the user's pulse too often, the consumption of the battery of the slave hearing aid 200 may be much greater than the consumption of the battery of the master hearing aid 100.

Therefore, when the pulse measurement period (wake-up period) of the slave hearing aid 200 is appropriately controlled in real time by monitoring and comparing a state of charge of the battery (not shown in the drawings) of the master hearing aid 100 with a state of charge of the battery (not shown in the drawings) of the slave hearing aid 200, the difference of the state of charge between the batteries of the master hearing aid 100 and the slave hearing aid 200 can be reduced.

According to an additional aspect of the present invention, the master hearing aid 100 or the slave hearing aid 200 may separately further include an audio mixer 170 or 280. The audio mixer 170 or 280 amplifies or attenuates the digital audio signal for the hearing aid or the digital audio signal for the wireless headset by a frequency channel and outputs the result.

The user of a hearing aid generally has hearing loss for audio signals in a high frequency band rather than a low frequency band. Therefore, the user may achieve improved quality for hearing audio through amplification or attenuation of the audio signal by a frequency channel, that is, relatively attenuating the digital audio signal for the hearing aid or the digital audio signal for the wireless headset in a low frequency band and relatively amplifying the digital audio signal for the hearing aid or the digital audio signal for the wireless headset in a high frequency band by the audio mixer 170 or 280.

Since multiple functions such as a wireless headset function, a function of measuring pulse, a function of transmitting the pulse information, etc. in addition to a hearing aid function are implemented in the binaural hearing aid of the present invention, user convenience can be improved.

The present invention can be utilized in technical fields of hearing aids and hearing aid applications.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A binaural hearing aid with multiple functions, comprising:

a master hearing aid; and a slave hearing aid,
wherein the master hearing aid comprises:
- a microphone configured to receive an analog audio signal from outside;
- a signal processing unit configured to amplify the analog audio signal input by the microphone, perform automatic gain control and AD conversion, and output a result;
- a first wireless communication unit configured to receive a digital audio signal from a smart device using a first wireless communication protocol;
- an ear speaker configured to output a digital audio signal for a hearing aid output by the signal processing unit or output a digital audio signal for the wireless headset received by the first wireless communication unit; and
- a control unit configured to control performance of a hearing aid function performed by the signal processing unit and a wireless headset function performed by the first wireless communication unit, and perform control such that the hearing aid function is stopped when a first wireless communication function is activated.

2. The binaural hearing aid of claim 1, wherein the master hearing aid further comprises a second wireless communication unit configured to transmit the digital audio signal for the wireless headset received by the first wireless communication unit to the slave hearing aid using a second wireless communication protocol.

3. The binaural hearing aid of claim 2, wherein the slave hearing aid comprises:
- a microphone configured to receive an analog audio signal from the outside;
- a signal processing unit configured to amplify the analog audio signal input by the microphone, perform automatic gain control and AD conversion, and output a result;
- a second wireless communication unit configured to receive a digital audio signal from the master hearing aid using a second wireless communication protocol;
- an ear speaker configured to output a digital audio signal for a hearing aid output by the signal processing unit or output a digital audio signal for the wireless headset received by the second wireless communication unit; and
- a control unit configured to control performance of a hearing aid function performed by the signal processing unit and a wireless headset function performed by the second wireless communication unit.

4. The binaural hearing aid of claim 3, wherein the slave hearing aid further comprises:
- a pulse measuring device configured to measure a pulse of a user; and
- a memory configured to locally store pulse information measured by the pulse measuring device.

5. The binaural hearing aid of claim 4, wherein the control unit of the slave hearing aid is further configured to perform a pulse measuring function of performing control such that the pulse of the user is measured using the pulse measuring device and the pulse information of the user is stored and accumulated in the memory.

6. The binaural hearing aid of claim 5, wherein the control unit of the slave hearing aid is further configured to control a pulse measurement period of the pulse measuring device by comparing a state of charge of a battery of the master hearing aid with a state of charge of a battery of the slave hearing aid.

7. The binaural hearing aid of claim 4, wherein the control unit of the slave hearing aid is further configured to perform a pulse information transmitting function of performing control such that the pulse information stored in the memory is read and the pulse information is transmitted to the master hearing aid through the second wireless communication unit of the slave hearing aid.

8. The binaural hearing aid of claim 7, wherein the control unit of the master hearing aid is further configured to perform a pulse information transmitting function of performing control such that the pulse information transmitted from the slave hearing aid is received through the second wireless communication unit of the master hearing aid and the pulse information is transmitted to the smart device through the first wireless communication unit.

9. The binaural hearing aid of claim 3, wherein the control unit of the master hearing aid is further configured to control a delay of an output of the digital audio signal for the wireless headset of the ear speaker of the master hearing aid to synchronize the output of the digital audio signal for the wireless headset of the ear speaker of the master hearing aid and the output of the digital audio signal for the wireless headset of the ear speaker of the slave hearing aid.

10. The binaural hearing aid of claim 3, wherein the master hearing aid or the slave hearing aid further comprises an audio mixer configured to amplify or attenuate the digital audio signal for the hearing aid or the digital audio signal for the wireless headset by a frequency channel, and output a result of the amplification or attenuation.

11. The binaural hearing aid of claim 1, wherein the control unit of the master hearing aid is further configured to transmit an instruction to stop a hearing aid function of the slave hearing aid through the second wireless communication unit of the master hearing aid when the first wireless communication function is activated.

12. The binaural hearing aid of claim 11, wherein a control unit of the slave hearing aid is configured to perform control such that the hearing aid function of the slave hearing aid is stopped when the instruction to stop the hearing aid function of the slave hearing aid is received.

* * * * *